United States Patent
Ostergaard et al.

(10) Patent No.: US 7,123,685 B2
(45) Date of Patent: Oct. 17, 2006

(54) DEVICE AND METHOD FOR ANALYZING FAT OF MEAT

(75) Inventors: Anders Ostergaard, Hoeng (DK); Jürgen Bernhardt, Biedenkopf-Weitenbach (DE)

(73) Assignee: Convenience Food Systems Wallau GmbH & Co. KG, Biedenkopf-Wallau (DE)

( * ) Notice: Subject to any disclaimer, the term of this patent is extended or adjusted under 35 U.S.C. 154(b) by 43 days.

(21) Appl. No.: 10/451,330

(22) PCT Filed: Nov. 20, 2001

(86) PCT No.: PCT/EP01/13428

§ 371 (c)(1),
(2), (4) Date: Dec. 15, 2003

(87) PCT Pub. No.: WO02/052257

PCT Pub. Date: Jul. 4, 2002

(65) Prior Publication Data

US 2004/0081275 A1 Apr. 29, 2004

(30) Foreign Application Priority Data

Dec. 22, 2000 (DE) .............................. 100 64 707

(51) Int. Cl.
G01N 23/083 (2006.01)
G01N 23/087 (2006.01)

(52) U.S. Cl. .................. 378/53; 378/57; 378/98.9

(58) Field of Classification Search ............. 378/53, 378/57, 98.9, 51, 58, 54, 55, 56
See application file for complete search history.

(56) References Cited

U.S. PATENT DOCUMENTS

| | | | | |
|---|---|---|---|---|
| 4,168,431 A | * | 9/1979 | Henriksen | 378/53 |
| 4,171,164 A | | 10/1979 | Groves et al. | 378/53 |
| 4,504,963 A | * | 3/1985 | Johnson | 378/53 |
| 4,844,619 A | | 7/1989 | Lesar et al. | 366/133 |
| 5,296,654 A | * | 3/1994 | Farley et al. | 177/145 |
| 5,585,603 A | * | 12/1996 | Vogeley, Jr. | 177/25.13 |
| 5,918,977 A | * | 7/1999 | Borggaard et al. | 366/140 |
| 6,107,809 A | | 8/2000 | Moshe et al. | 324/640 |

(Continued)

FOREIGN PATENT DOCUMENTS

DE 4215951 A1 11/1993

(Continued)

OTHER PUBLICATIONS

Patent Abstracts of Japan, Publication No. 09072774 A.

(Continued)

*Primary Examiner*—Allen C. Ho
(74) *Attorney, Agent, or Firm*—Perman & Green, LLP

(57) ABSTRACT

The invention relates to continuously determining the fat content of meat. A conveyor belt is used on which the pieces of meat to be examined are advanced past a radiation source serving as a fat analyzing means. The attenuation of an X-ray beam emitted from the radiation source is measured by a detector to determine the fat content. A weighing device continuously determines the weight of the quantity of meat located on the conveyor belt at the time of the measurement. This also makes it possible to calculate the absolute fat content. The invention also relates to a method for automatically setting a defined fat content in a mixer. The examined meat is transferred from the conveyor belt and into the mixer. The accumulated fat content in the mixer is calculated, compared with a set value, and the conveyor belt is loaded with lean or fatty meat according to the result of this calculation.

14 Claims, 1 Drawing Sheet

U.S. PATENT DOCUMENTS

Figure 1:
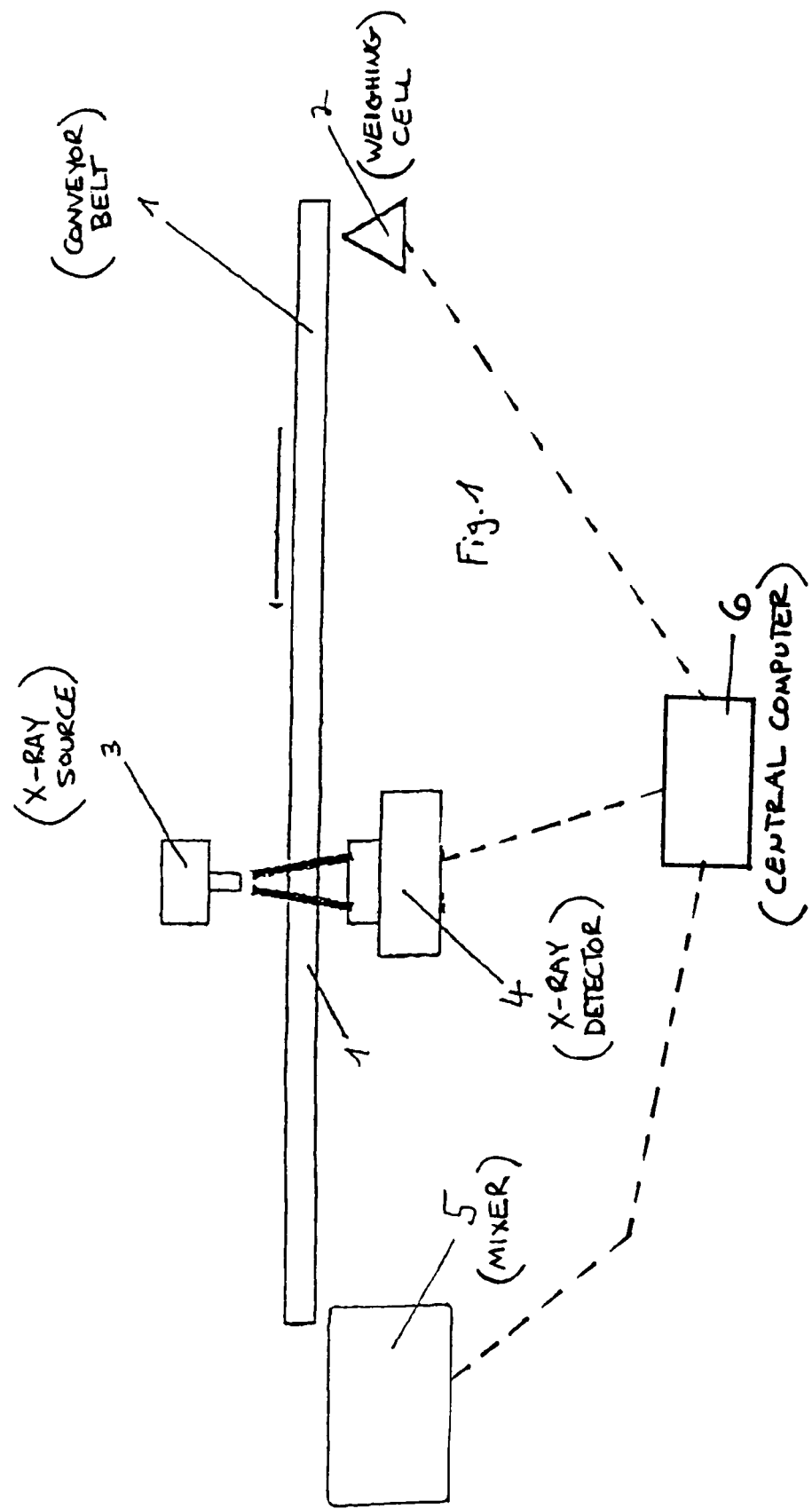

| | | | |
|---|---|---|---|
| 6,370,223 B1 * | 4/2002 | Gleason et al. | 378/58 |
| 6,597,759 B1 * | 7/2003 | Mazess et al. | 378/53 |
| 6,600,805 B1 * | 7/2003 | Hansen | 378/53 |
| 6,609,423 B1 * | 8/2003 | Retterath et al. | 73/433 |
| 6,648,501 B1 * | 11/2003 | Huber et al. | 366/301 |
| 6,678,396 B1 * | 1/2004 | Bartle | 382/110 |
| 2004/0149841 A1 * | 8/2004 | Linn et al. | 241/101.2 |
| 2005/0084064 A1 * | 4/2005 | McIntyre | 378/54 |
| 2005/0188859 A1 * | 9/2005 | Bruce et al. | 99/486 |
| 2005/0287252 A1 * | 12/2005 | Schrock et al. | 426/231 |

FOREIGN PATENT DOCUMENTS

| | | |
|---|---|---|
| DK | 172377 B1 | 4/1998 |
| EP | 0009214 A1 | 4/1980 |
| EP | 0012492 A1 | 6/1980 |
| GB | 2285126 A | 6/1995 |
| WO | WO 97/26533 | 7/1997 |
| WO | WO 01/29557 A3 | 4/2001 |
| WO | WO 01/96844 A1 | 12/2001 |

OTHER PUBLICATIONS

Patent Abstracts of Japan, Publication No. 09126871 A.

* cited by examiner

DEVICE AND METHOD FOR ANALYZING FAT OF MEAT

This application claims the benefit of the earlier filed International Application No. PCT/EP01/3428, International Filing Date, Nov. 20, 2001, which designated the United States of America, and which international application was published under PCT Article 21 (2) as WO Publication No. WO 02/052257.

The present invention relates to a device and a method for continuously determining the fat content of meat.

Since meat products must currently not exceed a defined fat content, exact analysis of meat fat and exact setting of defined fat contents in meat products is playing an every increasing role. The fat content of meat is frequently currently analyzed batchwise by taking a meat sample from a mixer or a conveyor belt that is then analyzed in a laboratory. The fat is also sometimes analyzed continuously by, for example, determining the fat content of meat on a conveyor belt using a sensor. However, these measurements have the disadvantage that the mass flow rate of the meat must be kept absolutely constant, and that the measurement takes place in a tube, which is generally unacceptable to the meat-processing industry, because the meat becomes smeared during this measurement. Furthermore, it is not possible to use this method in the analysis of fat in frozen meat.

It is therefore an object of the invention to provide a device and a method for continuously determining the fat content of meat, which method does not have the disadvantages of the prior art.

The object is achieved according to the invention by a device for continuously determining the fat content of meat having:

- a conveying means on which the meat is conveyed,
- a meat analysis means which continuously determines the fat content of the meat transported on the conveying means, and
- a weighing device by means of which the weight of the amount of meat situated on the conveyor belt at the time point of the measurement is continuously determined, so that even in the event of fluctuating meat conveying rates, at any time point, the fat content of the meat, based on the weight of the amount of meat situated on the conveyor belt at the time point of the measurement, can be determined.

In a preferred embodiment, the conveying means is a motor-driven conveyor belt, preferably a plastic conveyor belt, on which the meat is transported, for example, from a comminution device into a mixer, or to a comminution device, for example a mincer.

As fat analysis means, it is possible to use any fat analysis means familiar to those skilled in the art. Preferably, however, the fat analysis means has a source of radiation, preferably having a plurality of energy steps, and a radiation detector. In a very particularly preferred embodiment, the source of radiation is an X-ray source and the radiation detector is an X-ray detector. Preference as source of radiation is likewise given to an infrared source and, as radiation detector, to an infrared detector.

The direction of transmission of radiation through the meat is preferably perpendicularly to the transport direction, advantageously from above. Preferably, the height of the meat layer is 50 to 200 mm, particularly preferably 60 to 80 mm.

In the case of fat analysis using an X-ray detector, attenuation of the X-ray beam is measured, preferably in an energy range between 18 and 45 keV. Preferably, the distance between k-ray source and the X-ray detector is 150 to 300 mm, particularly preferably 200 to 240 mm. The transmitted radiation region is preferably a truncated cone which advantageously has a taper angle of 10 to 40°, particularly advantageously 15 to 35°. A microprocessor calculates the fat content and controls the X-ray source.

The weighing device in the inventive device is preferably belt scales.

By means of the inventive device, the fat content of fresh meat, frozen meat and/or a mixture thereof may be determined.

The inventive device has the advantage that the fat content of meat can be determined continuously without the mass flow rate of the meat needing to be constant. The inventive device can also determine the fat content of frozen meat. The device is simple to manufacture and simple to integrate into a meat production process. The measurement accuracy is ±1% by weight.

The present invention further relates to a method for continuously determining the fat content of meat using the inventive device in which the meat is passed by the fat analysis means by the conveying means with its fat content being determined continuously and in which, during determination of the fat content, the weight of the meat under test is measured continuously and on the basis of these data the fat content per unit weight of the meat under test is determined.

In a preferred embodiment of the inventive method, the values of the fat content and weight of the meat are determined over a period of 1 to 10 seconds, preferably 2 to 4 seconds.

Preferably, the fat content is determined after comminution of the meat and before the meat is mixed in a mixer with other meat types or with meat additives.

The inventive method has the advantage that it can be integrated simply and conveniently into an existing meat production process. In particular, it is also possible using the inventive method to measure the fat content at a non-constant transport rate. Using the inventive method it is possible to determine the fat content per weight of meat under test and to transfer the data to a central computer, so that, for example, the maximum fat content of the product can be reported on the product to be sold.

The present invention further relates to a method for automatically setting a defined fat content in a mixer using the inventive device, in which the meat is transported by the conveying means into the mixer, the method having any desired repetition of the following method steps:

a. determining the fat content and weight of the meat situated on the conveying means, b. calculating the mean fat content of the meat in the mixer using the results from point a., c. comparing the results from b. with a preset value for the fat content of the meat in the mixer, where c1 at too high a fat content the conveying means is charged with lean meat and c2 at too low a fat content the conveying means is charged with fat meat.

Preferably, the mean fat content of the meat in the mixer is calculated using the following formula:

$$\frac{(\text{fat content }\%_1 \cdot \text{weight}_1 + \text{fat content }\%_2 \cdot \text{weight}_2 + \ldots + \text{fat content }\%_n \cdot \text{weight}_n)}{\sum_{i=1}^{n} \text{weight }(n)}.$$

Likewise preferably, the values of fat content and weights of the meat are averaged over a period of 1 to 10 seconds, preferably 2 to 4 seconds.

This inventive method has the advantage that the fat content can be set very accurately in a mixer. According to the invention it is possible to determine the fat content of the meat in the mixer accurately at any time point and accordingly to correct the fat content of the meat still to be conveyed into the mixer. This gives time savings for the manufacturer.

The invention will be explained below with reference to FIG. 1. These explanations are merely by way of example and do not restrict the general inventive concept.

FIG. 1 shows the inventive device for continuously determining the fat content of meat. The device consists of a conveyor belt 1, a weighing cell 2, an X-ray source 3 and an X-ray detector 4. The meat is passed by the X-ray source by means of the conveyor belt (direction of motion indicated by the arrow) and X-rays are transmitted through the meat. The X-ray detector measures the absorption of the X-rays by the meat and, on the basis of this information, can determine the fat content. At the same time, during the measurement, the weight of the meat which is situated on the conveyor belt at the time point of measurement is measured and as a result the amount of meat having the measured fat content is determined. These data are transmitted to a central computer 6 so that either the exact fat content of a defined product can be determined or these data can be used to calculate the fat content, for example in a mixer. The central computer 6 also takes over control of the X-ray source and/or of the X-ray detector.

The inventive device has proved to be very robust and, using it, it is possible to set the fat content per unit weight very exactly.

The invention claimed is:

1. A device for continuously determining a fat content of meat having:
   a mixer, the meat being mixed with other meat or with meat additives in the mixer;
   a conveyor belt on which the meat is conveyed to the mixer,
   a fat analysis means comprising a radiation source and a radiation detector, which continuously determines the fat content of the meat transported on the conveyor belt,
   a weighing device comprising belt scales by means of which the weight of an amount of meat situated on the conveyor belt at the time point of a measurement is continuously determined, and
   a central computer adapted to determine the fat content of the meat at any point in time, even in the event of fluctuating meat conveying rates, based on the weight of the amount of meat on the conveyor belt at the time point of the measurement, the central computer being configured to calculate a mean fat content of the meat in the mixer.

2. The device as claimed in claim 1, characterized in that the conveyor belt is a motor-driven conveyor belt.

3. The device as claimed in claim 2, characterized in that the conveyor belt is a plastic conveyor belt.

4. The device as claimed in claim 1, characterized in that the fat analysis means is a radiation source having a plurality of energy steps and a radiation detector.

5. The device as claimed in claim 4, characterized in that the radiation source having a plurality of energy steps is an X-ray source and the radiation detector is an X-ray detector.

6. The device as claimed in claim 5, characterized in that the X-ray source emits an X-ray beam and that an attenuation of the X-ray beam is measured.

7. The device as claimed in claim 6, characterized in that the energy of the X-ray beam is in the energy range from 18 to 45 Kev.

8. The device as claimed in claim 1, characterized in that the meat is fresh meat and/or frozen meat.

9. The device as claimed in claim 8, characterized in that the fresh meat and/or frozen meat is ground.

10. A method for determining a fat content of a meat product, comprising the steps:
    conveying meat on a conveyor belt from a comminution device to a mixer;
    mixing the meat in the mixer with other types of meat or with meat additives;
    continuously determining a fat content of meat passing by a fat analysis means on the conveyor belt by emitting a radiation beam from a radiation source through the meat and measuring the attenuation of the radiation beam by means of a radiation detector;
    continuously measuring the weight of an amount of meat situated on the conveyor belt by a weighing device at the time point of the determination of the fat content, wherein the weighing device comprises belt scales;
    calculating the fat content per unit weight of the meat on the basis of the measured fat content and measured weight; and
    calculating the fat content of the meat product in the mixer.

11. The method as claimed in claim 10, characterized in that the values of the fat content and weight of the meat are averaged over a period of 1–10 seconds.

12. A method for automatically setting a defined fat content of a meat product in a mixer comprising any desired repetition of the following method steps:
    determining the fat content of the meat product in the mixer according to the method of claim 10;
    comparing the calculated fat content of the meat product in the mixer with a preset value for the fat content of the meat product in the mixer, where
    at too high a fat content the conveyor belt is charged with lean meat and
    at too low a fat content the conveyor belt is charged with fat meat.

13. The method as claimed in claim 12, characterized in that a mean fat content of the meat in the mixer is calculated according to the following formula:

(fat content $\%_1$ weight$_1$+fat content $\%_2$*weight$_2$+ . . . +fat content $\%_n$ weight$_n$)/(weight$_1$+weight$_2$+ . . . weight$_n$).

14. The method as claimed in claim 12, characterized in that the values of the fat content and the weight of the meat are averaged over a period of 1–10 seconds.

* * * * *